United States Patent
Beggs et al.

(10) Patent No.: US 11,684,715 B2
(45) Date of Patent: Jun. 27, 2023

(54) CONTACT SENSOR FOR MONITORING MEDICATION ADHERENCE

(71) Applicant: HIVE Medical, Inc., Saint Louis, MO (US)

(72) Inventors: Joseph Matthew Beggs, Saint Louis, MO (US); Christopher James Sleckman, Saint Louis, MO (US); Glen Robert Kleinschmidt, Saint Louis, MO (US); Aravindh Shanmuganathan, Saint Louis, MO (US)

(73) Assignee: Hive Medical, Inc., Saint Louis, MO (US)

( * ) Notice: Subject to any disclaimer, the term of this patent is extended or adjusted under 35 U.S.C. 154(b) by 615 days.

(21) Appl. No.: 16/846,012

(22) Filed: Apr. 10, 2020

(65) Prior Publication Data

US 2020/0324047 A1 Oct. 15, 2020

Related U.S. Application Data

(60) Provisional application No. 62/832,058, filed on Apr. 10, 2019.

(51) Int. Cl.
*A61M 5/168* (2006.01)
*G01D 5/16* (2006.01)

(52) U.S. Cl.
CPC .......... *A61M 5/16886* (2013.01); *G01D 5/16* (2013.01); *A61M 2205/14* (2013.01); *A61M 2205/332* (2013.01); *A61M 2205/3327* (2013.01); *A61M 2205/3553* (2013.01); *A61M 2205/3561* (2013.01); *A61M 2205/3584* (2013.01); *A61M 2205/50* (2013.01)

(58) Field of Classification Search
CPC ........ A61M 2205/14; A61M 2205/332; A61M 2205/3327; A61M 2205/3553; A61M 2205/3561; A61M 2205/3584; A61M 2205/50; A61M 5/16886; G01D 5/16
See application file for complete search history.

(56) References Cited

U.S. PATENT DOCUMENTS

| | | | |
|---|---|---|---|
| 3,876,234 A * | 4/1975 | Harms | A61M 39/10 285/332 |
| 5,429,614 A * | 7/1995 | Fowles | A61J 1/2089 604/88 |
| 7,727,194 B2 | 6/2010 | Nalagatia et al. | |
| 8,747,348 B2 * | 6/2014 | Yodfat | A61M 5/14248 604/67 |
| 8,870,818 B2 * | 10/2014 | Alderete, Jr. | G01R 33/00 324/750.16 |
| 9,039,659 B2 * | 5/2015 | Hanson | A61M 5/14248 324/207.21 |
| 9,452,255 B2 * | 9/2016 | Tieck | A61M 39/1011 |
| 9,480,455 B2 | 11/2016 | Buckberry | |
| 9,533,092 B2 | 1/2017 | Gyrn | |
| 9,752,914 B2 * | 9/2017 | Levine | G01F 1/56 |
| 10,293,119 B2 | 5/2019 | Caspers et al. | |
| 10,857,287 B2 * | 12/2020 | Damiano | A61M 5/14566 |
| 2016/0015886 A1 * | 1/2016 | Pananen | A61M 5/1456 604/111 |
| 2019/0326012 A1 | 10/2019 | Witt | |

* cited by examiner

*Primary Examiner* — Quynh-Nhu H. Vu

(74) *Attorney, Agent, or Firm* — Polsinelli PC

(57) ABSTRACT

Systems, devices, and methods described herein monitor when the fluid path of a medication in a parenteral medication delivery device is established or interrupted.

20 Claims, 8 Drawing Sheets

CONTACT SENSOR FOR MONITORING MEDICATION ADHERENCE

CROSS-REFERENCE TO RELATED APPLICATIONS

This application claims the benefit of U.S. Provisional Patent Application No. 62/832,058 filed Apr. 10, 2019, the entire disclosure of which is incorporated herein by reference.

FIELD OF THE INVENTION

The present disclosure provides systems, devices, and methods to monitor a fluid flow path between a medication reservoir and a medication dispense assembly in a medication delivery device.

BACKGROUND OF THE INVENTION

In the medical field one of the largest challenges with at-home medication is the issue of non-adherence caused by patients, either advertently or inadvertently, not following their prescribed medication regimen. This non-adherence includes but is not limited to patients failing to take medication at the prescribed times of day, for the prescribed duration of time and/or for the prescribed number of times per day. Outpatient care is typically much less expensive than inpatient care, and as a result, healthcare providers have drastically increased the proportion of patients receiving outpatient care compared to inpatient care over the past few decades. However, with reduced oversight from providers (i.e. doctors and nurses), non-adherence has become a more prevalent problem. Therefore, a method to objectively monitor outpatient medication regimen adherence is useful.

Currently, the only consistent methods for dealing with outpatient non-adherence are with house visits and phone calls. The latter has limited effectiveness and both take time and resources that could be more efficiently allocated and administered. As the median age of people in the United States continues to increase the need for a system of monitoring patient adherence will also become more valuable. Conventional solutions have put the onus on the non-adherent patients to do extra work in order for these solutions to monitor adherence, but this is not effective because non-adherent patients typically do not go out of their way to follow extra directions.

SUMMARY OF THE INVENTION

One aspect of the present disclosure encompasses a system for monitoring a state of a fluid flow path between a medication reservoir and a medication dispense assembly in a medication delivery device. The system comprises (a) an electrical contact sensor attached to the medication delivery device at a connector between the medication reservoir and the medication dispense assembly and operable to communicate a state of an electrical connection, the electrical contact sensor comprising an enclosure comprising a first electrical contact, a second electrical contact, and a first spring operable to bias the first and second contacts from establishing the electrical connection, wherein the state of the electrical connection is a presence or absence of the electrical current; and (b) a controller in electrical communication with the contact sensor, the controller comprising an input component operable to receive the state of the electrical connection communicated by the sensor and at least one processor operable to assign one or more event times, wherein each event time indicates the time of a change in the state of the electrical connection. A force applied to the contact sensor to connect the medication reservoir with the dispense assembly causes the contact of the first and second electrical contacts thereby establishing the electrical connection between the first and second contact sensors, and wherein an electrical connection signals the connection of the medication reservoir with the dispense assembly and formation of the fluid flow path between the medication reservoir and dispense assembly and the absence of an electrical connection signals disconnection of the medication reservoir with the dispense assembly.

The enclosure can comprise an elongated body comprising a cavity, a proximal surface comprising a top surface, a bottom surface, and an orifice extending from the top surface to the bottom surface, and a distal opening; and a support comprising a distal surface, a proximal surface, a perimeter complementary to an inside perimeter of the enclosure, an orifice extending from the distal surface to the proximal surface of the support, wherein the orifice is concentric with the orifice in the body, forming a channel extending from the orifice in the enclosure to the orifice in the support, wherein the support is operable to be displaced along a longitudinal axis within the enclosure. The contact sensor can be attached to the medication device through the channel extending from the orifice in the enclosure to the orifice in the support. The first electrical contact and the second electrical contact can be attached to the proximal surface of the support in a shape operable to surround the orifice in the support. The first spring can surround the channel and extend from the bottom surface of the enclosure to the proximal surface of the support, and the spring can be operable to bias the support from the bottom surface of the enclosure.

The enclosure can further comprise an electrically conductive ring attached to the bottom surface of the body. The conductive ring can be operable to contact and establish an electrical connection between the first and second electrical contacts when a force applied to the enclosure and/or support to connect the medication reservoir with the dispense assembly through the channel causes the enclosure and/or support to be displaced along the longitudinal axis. The electrical connection signals the connection of the medication reservoir with the dispense assembly and the formation of the fluid flow path between the medication reservoir and dispense assembly. The conductive ring can be a finger disk spring.

The medication delivery device can further comprise a first section of tubing comprising a first end and a second end, wherein the first end of the first section of tubing is attached to and in fluid communication with the medication reservoir, and a second section of tubing comprising a first end and a second end, wherein the first end of the second section of tubing is attached to and in fluid communication with the medication delivery device, and wherein each of the second end of the first section of tubing and the second end of the second section of tubing comprise a connector for connecting the second ends of the sections of tubing, thereby forming a fluid flow path between the medication reservoir and the dispense assembly. The contact sensor can be attached at a connector between the medication reservoir and the first end of the first section of tubing, at a connector between the dispense assembly and the first end of the second section of tubing, or at the connector for connecting the second ends of the sections of tubing. The connector can be a luer connector.

The system can be further operable to communicate the one or more event times to an individual. The controller can further be operable to communicate the one or more event times to an individual. The individual can be a patient, a caretaker for the patient, an individual monitoring administration of the medication to a subject, or any other entity designated by one of the aforementioned. The controller can also be operable to communicate the one or more event times to a secondary device. The controller can further comprise a transmitter operable to communicate the one or more event times to the secondary device wirelessly using a wireless communication protocol. The wireless communication protocol is selected from an NFC communication, a Radio-frequency identification (RFID) communication, Bluetooth, LTE, ZigBee, LoraWAN, or Wi-Fi. In some aspects, the wireless communication protocol is Bluetooth.

The secondary device can be a mobile computing device such as a cellular phone, a portable computer, a wearable device, a portable computer with no user interface, and/or a personal digital assistant (PDA). The secondary device can also be a cloud computing device.

The dispense assembly can be an intravenous dispense assembly. For instance, the dispense assembly is peripherally inserted central catheter (PICC line).

Another aspect of the present disclosure encompasses an electrical contact sensor device for monitoring a state of a fluid flow path between a medication reservoir and medication dispense assembly in a medication delivery device. The device comprises an enclosure comprising a first electrical contact and a second electrical contact and a first spring operable to bias the first and second contacts from establishing an electrical connection. The state of the electrical connection is a presence or absence of the electrical connection. A force applied to the contact sensor to connect the medication reservoir with the dispense assembly causes the contact of the first and second electrical contacts thereby establishing a connection between the first and second contact sensors, and the electrical connection signals the connection of the medication reservoir with the dispense assembly and formation of the fluid flow path between the medication reservoir and dispense assembly and the absence of an electrical connection signals disconnection of the medication reservoir with the dispense assembly.

The enclosure can comprise an elongated body comprising a cavity, a proximal surface comprising a top surface, a bottom surface, and an orifice extending from the top surface to the bottom surface, and a distal opening; and a support comprising a distal surface, a proximal surface, a perimeter complementary to an inside perimeter of the enclosure, an orifice extending from the distal surface to the proximal surface of the support, wherein the orifice is concentric with the orifice in the body, forming a channel extending from the orifice in the enclosure to the orifice in the support, wherein the support is operable to be displaced along a longitudinal axis within the enclosure. The contact sensor can be attached to the medication device through the channel extending from the orifice in the enclosure to the orifice in the support.

The first electrical contact and the second electrical contact can be attached to the proximal surface of the support in a shape operable to surround the orifice in the support. The first spring can surround the channel and extends from the bottom surface of the enclosure to the proximal surface of the support, and the spring can be operable to bias the support from the bottom surface of the enclosure.

The enclosure can further comprise an electrically conductive ring attached to the bottom surface of the body, wherein the conductive ring is operable to contact and establish an electrical connection between the first and second electrical contacts when a force applied to the enclosure and/or support to connect the medication reservoir with the dispense assembly through the channel causes the support, the enclosure, or both, to be displaced along the longitudinal axis, wherein an electrical connection signals the connection of the medication reservoir with the dispense assembly and the formation of the fluid flow path between the medication reservoir and dispense assembly. The conductive ring can be a finger disk spring.

The medication delivery device can further comprise a first section of tubing comprising a first end and a second end, wherein the first end of the first section of tubing is attached to and in fluid communication with the medication reservoir, and a second section of tubing comprising a first end and a second end, wherein the first end of the second section of tubing is attached to and in fluid communication with the medication delivery device, and wherein each of the second end of the first section of tubing and the second end of the second section of tubing comprise a connector for connecting the second ends of the sections of tubing, thereby forming a fluid flow path between the medication reservoir and the dispense assembly. The contact sensor can be attached through the channel at a connector between the medication reservoir and the first end of the first section of tubing, at a connector between the dispense assembly and the first end of the second section of tubing, or at the connector for connecting the second ends of the sections of tubing. The connector can be a luer connector.

BRIEF DESCRIPTION OF THE FIGURES

The description will be more fully understood with reference to the following figures, which are presented as various embodiments of the disclosure and should not be construed as a complete recitation of the scope of the disclosure, wherein.

DETAILED DESCRIPTION

Figure 1:
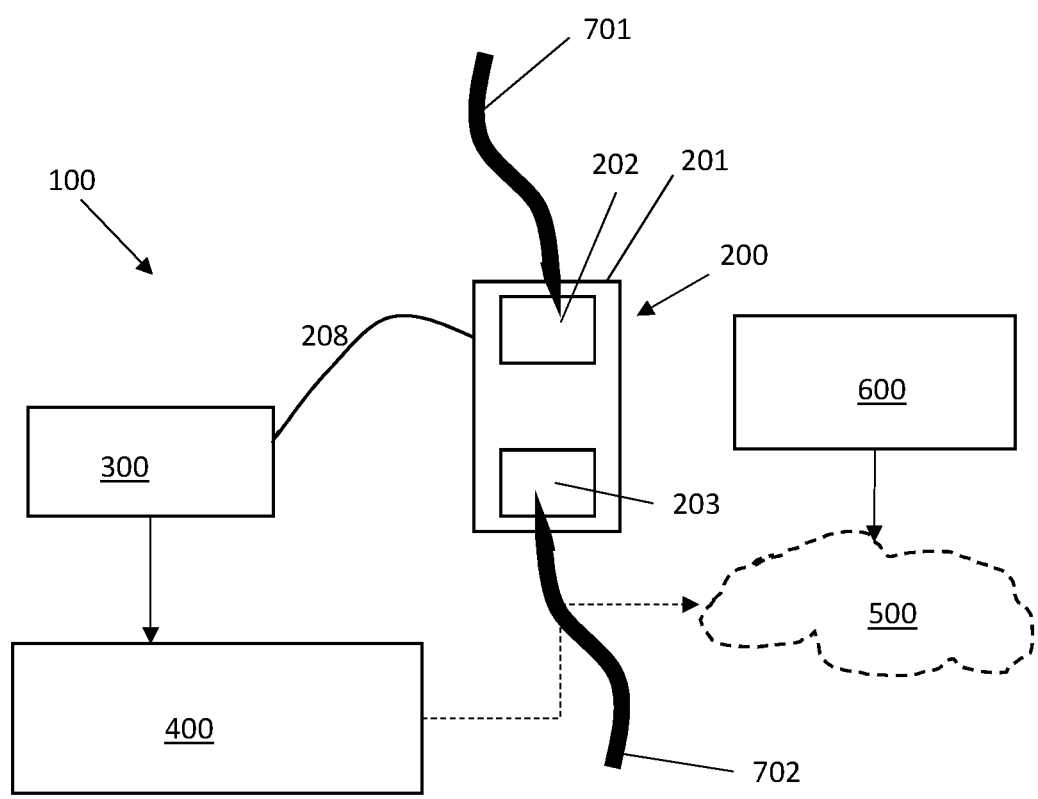
FIG. 1 illustrates a diagram of an aspect of a system in accordance with an aspect of the invention.

The systems, devices, methods, and computer program products for monitoring a fluid flow path will be understood from the accompanying drawings, taken in conjunction with the accompanying description. It is noted that, for purposes of illustrative clarity, certain elements in various drawings may not be drawn to scale. Several variations of the system are presented herein. It should be understood that various components, parts, and features of the different variations may be combined together and/or interchanged with one another, all of which are within the scope of the present application, even though not all variations and particular variations are shown in the drawings. It should also be understood that the mixing and matching of features, elements, and/or functions between various variations is expressly contemplated herein so that one of ordinary skill in the art would appreciate from this disclosure that the features, elements, and/or functions of one variation may be incorporated into another variation as appropriate, unless described otherwise.

Provided herein are systems, devices, methods, and computer program products for monitoring a fluid flow path of a medication for parenteral administration from a medication reservoir to a subject in need thereof. Parenteral administration can be subcutaneous, intramuscular, intraperitoneal, or intravenous administration.

In some aspects, systems disclosed herein monitor intravenous (IV) administration of medication by an IV administration device. In one aspect, the IV administration is an infusion of a medication. An IV infusion is a controlled administration of medication into your bloodstream over time. The infusion can be through standard IV lines. Standard IV lines are typically used for short-term needs. For instance, they may be used during a short hospital stay or in an outpatient setting to administer medication during surgery or to give pain medications, nausea medications, or antibiotics. A standard IV line can typically be used for up to four days. With standard IV administration, a needle can be inserted into a vein in the wrist, elbow, or the back of the hand. The catheter is then pushed over the needle. The needle is removed, and the catheter remains in your vein. All IV catheters are typically given in a hospital or clinic, or for outpatient IV therapy. Infusion can be pump infusion wherein a pump is attached to an IV line to send medication and a solution, such as sterile saline, into your catheter in a slow, steady manner. Pumps may be used when the medication dosage must be precise and controlled. Alternatively, infusion can be drip infusion. This method uses gravity to deliver a constant amount of medication over a set period of time. With a drip, the medication and solution drip from a bag through a tube and into the catheter.

An infusion can also be through a central venous catheter. Long-term medication treatment, such as chemotherapy or total parenteral nutrition, usually requires a central venous catheter (CVC) instead of a standard IV catheter. A CVC is inserted into a vein in your neck, chest, arm, or groin area. A CVC can stay in place for several weeks or even months. A CVC can be a peripherally inserted central catheter (PICC). A PICC has a long line that sends medication from the area of insertion, through your blood vessels, all the way to a vein near your heart. A PICC is typically placed in a vein above your elbow in your upper arm. A CVC can also be a tunneled catheter. With a tunneled catheter, medication can be sent directly into blood vessels in the heart. One end of the catheter is placed into a vein in the neck or chest during a short surgical procedure. The rest of the catheter is tunneled through the body, with the other end coming out through the skin. Medications can then be given into that end of the catheter. Additionally a CVC can be an implanted port. Like a tunneled catheter, an implanted port inserts a catheter into a vein in the neck or chest. This device is also placed during a short surgical procedure. But unlike a tunneled catheter, an implanted port is located completely beneath the skin. To use this device, a healthcare provider injects medication through the skin into the port, which sends the medication into the bloodstream.

The systems, devices, methods, and computer program products, allow for monitoring when and for how long the patient is using the apparatus for the parenteral administration of medication. Monitoring administration allows interested parties (e.g., medical professionals, patient caregivers, patient family and friends, etc.) be kept up to date on the patient's adherence. Practical uses for this information include but are not limited to: determining which patients need check-ups (e.g., in person, via telephone, via Internet such as instant messaging or video conference, etc.) to adjust their habits of usage, alerting physicians to patients who may be potentially abusing their medical devices, and/or tracking the non-adherence of patients, which would allow insurance companies and healthcare professional to determine which patients are more at-risk. One advantage of the systems and methods described herein includes providing objective verification of medication adherence of Outpatient Parenteral Antibiotic Therapy (OPAT) patients. The systems and methods described herein require minimal effort from patients, and this is particularly important for non-adherent patients. The systems, devices, and methods described herein also benefit from a simple and inexpensive design.

Figure 3:
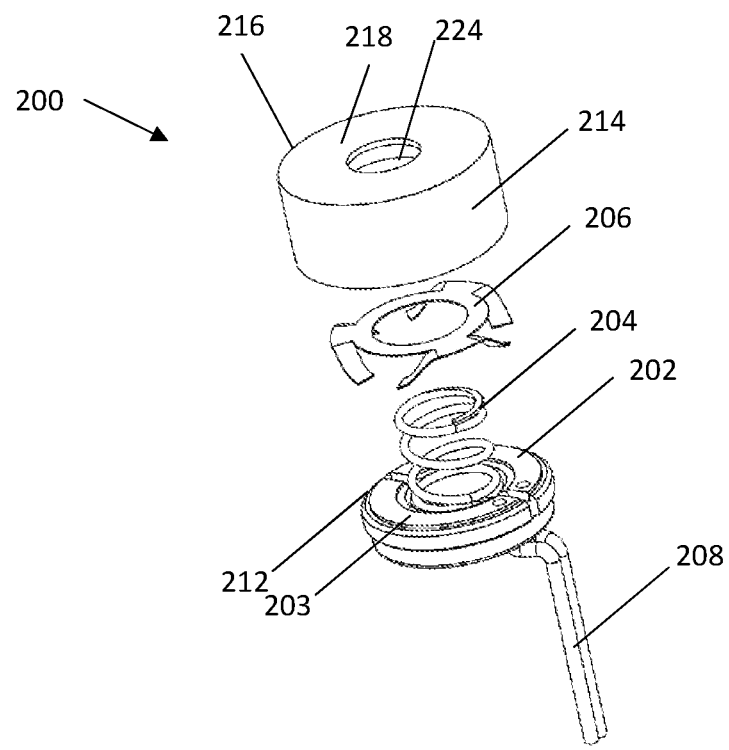
FIG. 3 is an exploded perspective view of an aspect of a contact sensor.
Figure 4:
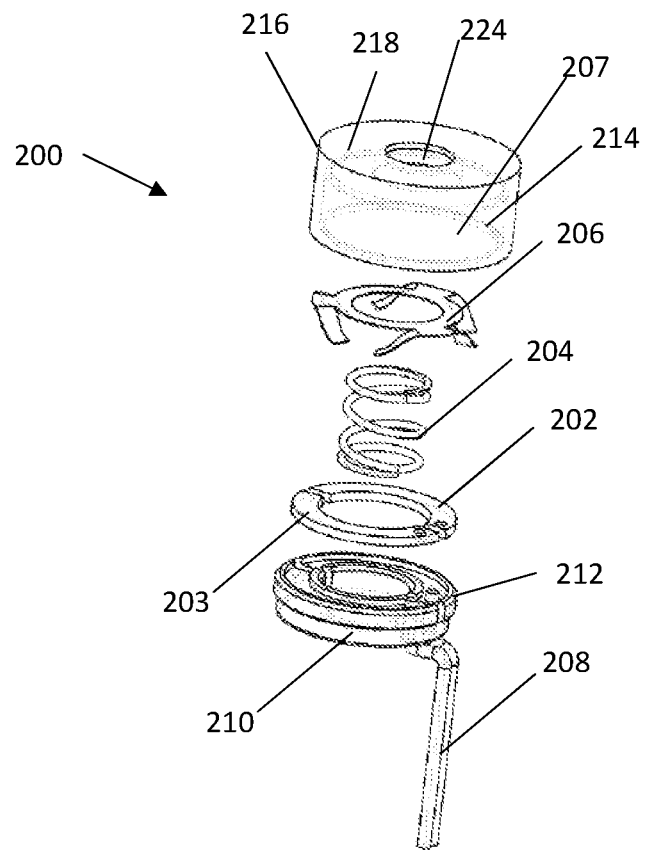
FIG. 4 is an exploded perspective view of an aspect of a contact sensor.

Referring to FIG. 1, one aspect of the system 100 is presented in accordance with an example in which a contact sensor 200 for attachment to a medication delivery device. The device can be removably attached to the medication delivery device. The electrical contact sensor 200 comprises an enclosure 201 comprising a first electrical contact 202, a second electrical contact 203, and a first spring 204 (shown in FIG. 3) operable to bias the first and second contacts from establishing an electrical connection. As shown in FIG. 1, system 100 further comprises a controller 300 in electrical communication with the contact sensor 200 through electrical wiring 208. A secondary device 400 may be in communication with the controller 300 of system 100. A cloud database 500 may also be in communication with the controller 300 or the secondary device 400 where one or more time events and/or states of the fluid flow path is stored for access by an individual of interest through an API 600. The individual can be the patient, or an individual monitoring the administration of the medication to the subject, such as a caretaker. Tubing 701 and 702 are shown attached to the contact sensor 200.

Figure 2:
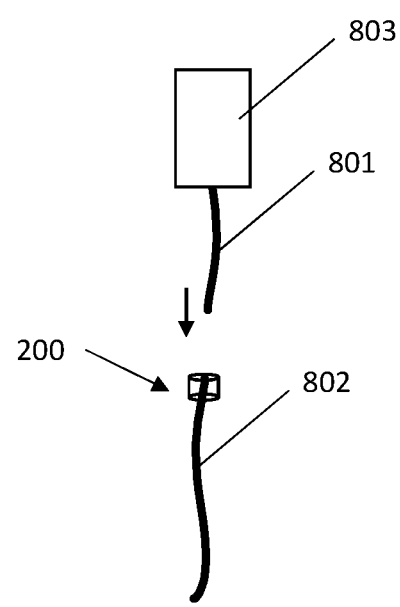
FIG. 2 is a diagram of an example of a contact sensor attached to a first section of an IV line at a connector before attaching the first section of the IV line with a second section of the IV line at the connector. A medication reservoir attached to the second section of the IV line is shown.

Referring to FIG. 2, the figure shows an example of a contact sensor 200 attached to a first end of a first section 802 of an IV line at a connector (not shown). A medication delivery device (not shown) is connected to a second end of the first section 802. Also shown is a second section 801 of an IV line. A medication reservoir 803 attached to the second section 801 of the IV line is shown. The figure shows the contact sensor and the IV lines before connecting the first and second sections of the IV line. The device and IV lines are shown before attaching the first section 702 of the IV line with the second section 801 of the IV line at the connector. The arrow shows the direction of the fluid flow path from the medication reservoir 803 to the medication delivery device.

Referring now to FIGS. 3-6, an aspect of the contact sensor 200 is shown. The electrical contact sensor 200 comprises an enclosure 201. The enclosure 201 comprises an elongated body 214 comprising a cavity, a proximal surface 216 comprising a top surface 218, a bottom surface 205, and an orifice 224 extending from the top surface 218 to the bottom surface 205. The body 214 comprises a distal opening 207. The enclosure 201 also comprises a support 210 comprising a distal surface 211, a proximal surface 212, a perimeter complementary to the inside perimeter of the enclosure, an orifice 213 extending from the distal surface 211 to the proximal surface 212 of the support 210. The orifice 213 is concentric with the orifice 224 in the body 214, forming a channel extending from the orifice 224 in the body 214 to the orifice 213 in the support 210. The support 210 is operable to be displaced along a longitudinal axis within the cavity of the body 214. In the aspect of the contact sensor 200 depicted in FIG. 2 and FIG. 3, the first electrical contact 202 and the second electrical contact 203 are attached to the proximal surface 212 of the support 210 in a shape operable to surround the orifice 213 in the support. The first spring 204 is shown, surrounding the channel and extending from the bottom surface 205 of the body 214 to the proximal surface 212 of the support 210. The spring 204 is operable to bias the support 210 from the bottom surface 205 of the body 214. The spring can be a compression spring, an extension spring, a torsion spring, a constant force spring, or a washer spring. In one aspect, the spring is a compression spring.

In the aspect of the contact sensor 200 depicted in FIGS. 3-6, the enclosure 201 further comprises an electrically conductive ring 206 attached to the bottom surface 205 of the body 214. The conductive ring 206 is operable to contact and establish an electrical connection between the first electrical contact 202 and second electrical contact 203 when a force applied to the body 214 and/or support 210 to connect the medication reservoir with the dispense assembly through the channel causes the support 210 to compress the first spring 204 and be displaced along the longitudinal axis of the enclosure 201. The formation of an electrical connection signals the connection of the medication reservoir with the dispense assembly and the formation of the fluid flow path between the medication reservoir and dispense assembly. In some aspects, the conductive ring 206 is a finger disk spring.

The electrical contact sensor 200 is attached at a connector. In some aspects, the medication delivery device further comprises a first section of tubing 801 comprising a first end and a second end, wherein the first end of the first section of tubing is attached to and in fluid communication with the medication reservoir, and a second section of tubing 802 comprising a first end and a second end, wherein the first end of the second section of tubing is attached to and in fluid communication with the medication delivery device, and wherein each of the second end of the first section of tubing and the second end of the second section of tubing comprise a connector for connecting the second ends of the sections of tubing, thereby forming a fluid flow path between the medication reservoir and the dispense assembly. In an aspect, the contact sensor is attached at a connector between the medication reservoir and the first end of the first section of tubing. In another aspect, the contact sensor is attached at a connector between the dispense assembly and the first end of the second section of tubing. In yet another aspect, the contact sensor is attached at the connector for connecting the second ends of the sections of tubing.

In some aspects, the contact sensor is removably attached to a connector. The contact sensor can be attached around the outside surface of the connector. Alternatively, the contact sensor can be attached within a housing of the connector. It should be noted however, that a contact sensor of the disclosure does not form a part of and is not in contact with the fluid flow path.

Connectors can be any fitting appropriate for use with a peritoneal medication delivery device, such as luer tapers.

The system further comprises a controller 300 in electrical communication with the contact sensor 200 through electrical wiring 208. As explained above, the state of the electrical connection is the presence or absence of the electrical connection. The controller 300 comprises an input controller operable to receive the state of the electrical connection communicated by the sensor and at least one processor operable and assign one or more event times. Each event time indicates the time of a change in the state of the connection.

The controller 300 can be operable to communicate the one or more event times to an individual. For instance, the controller 300 can further comprise an output component to indicate a time event to an individual. Alternatively, the controller 300 can communicate the one or more event times to a secondary device 400. For example, the output component can be a transmitter operable to communicate the one or more event times to a secondary device 400 wirelessly using a wireless communication protocol.

Figure 7:
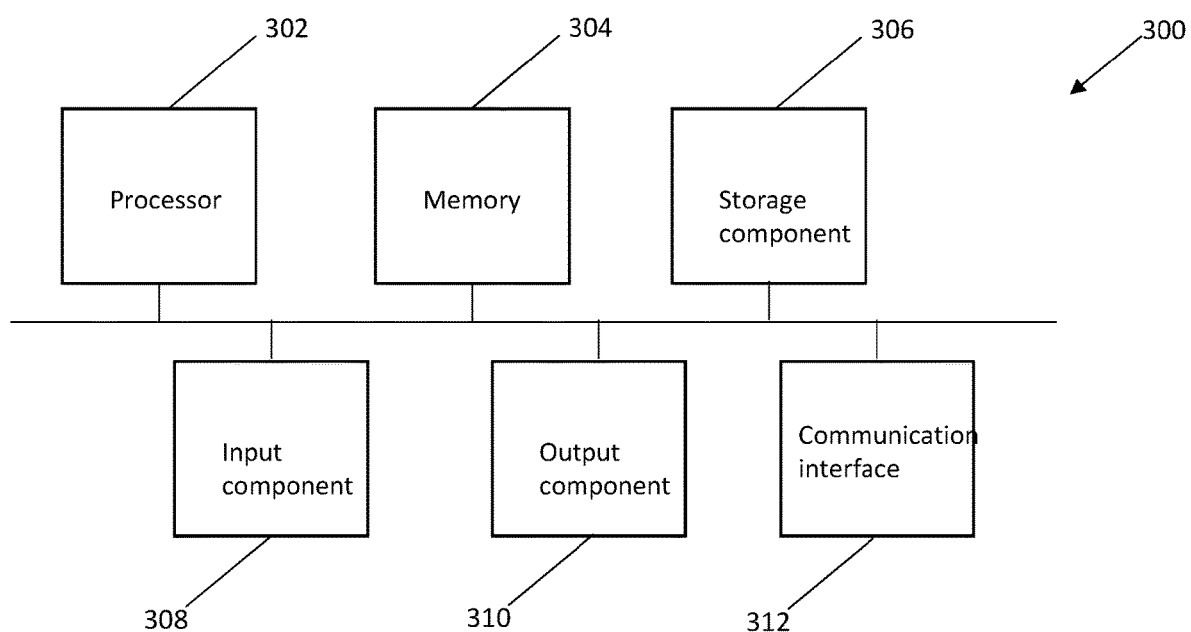
FIG. 7 is a diagram of an aspect of components of a controller.

Referring now to FIG. 7, FIG. 7 is diagram of components in accordance with an example controller 300. The controller 300 is provided by way of example, as the controller 300 can comprise other components, such as a transmitter, a computer monitor etc., that may be present for functioning of the controller in various aspects of the disclosure. Each block shown in FIG. 7 represents one or more component of controller 300. Furthermore, the illustrated order of blocks is illustrative only and the order of the blocks can change according to the present disclosure. Additional blocks may be added or fewer blocks may be utilized, without departing from this disclosure.

The example controller 300 shows the at least one processor 302. The controller 300 shown in FIG. 7 further comprise memory 304, storage component 306, input component 308, output component 310, and communication interface 312. A power source can provide power to the controller 300.

Memory 304 may include a random-access memory (RAM), a read only memory (ROM), and/or another type of dynamic or static storage device (e.g., a flash memory, a magnetic memory, an optical memory, etc.) that stores information and/or instructions for use by controller 300.

Storage component 306 may store information and/or software related to the operation and use of controller 300. For example, storage component 306 can include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

In addition to the input component 308 operable to receive the state of the electrical connection communicated by the sensor, the controller 300 can include addition input components that permits input by a user (e.g., a touch screen display, a keyboard, a keypad, a mouse, a button, a switch, a microphone, etc.).

Output component 310 may include a component that provides output information from controller 300 (e.g., a display, a speaker, one or more light-emitting diodes (LEDs), etc.).

Communication interface 312 may include a transceiver-like component (e.g., a transceiver, a separate receiver and transmission source, etc.) that enables controller 300 to communicate the one or more event times to a secondary device, such as via a wireless connection using a wireless communication protocol, a wired connection, or a combination of wired and wireless connections. A wired connection can include an Ethernet interface, an optical interface, a coaxial interface, an infrared interface, a universal serial bus (USB) interface, and/or the like. A wireless communication protocol can include an NFC communication, a Radio-frequency identification (RFID) communication, Bluetooth, LTE, ZigBee, LoraWAN, Wi-Fi, and/or the like.

The secondary device 400 can be a stationary computing device such as a desktop computer. Alternatively, the secondary device 400 can be mobile computing device such as a cellular phone (e.g., a smartphone or standard cellular phone), a portable computer (e.g., a tablet computer, a laptop computer, etc.), a wearable device (e.g., a watch, a pair of glasses, a lens, clothing, and/or the like), a personal digital assistant (PDA), a computing device with no user interface, and/or other like devices.

Figure 5:
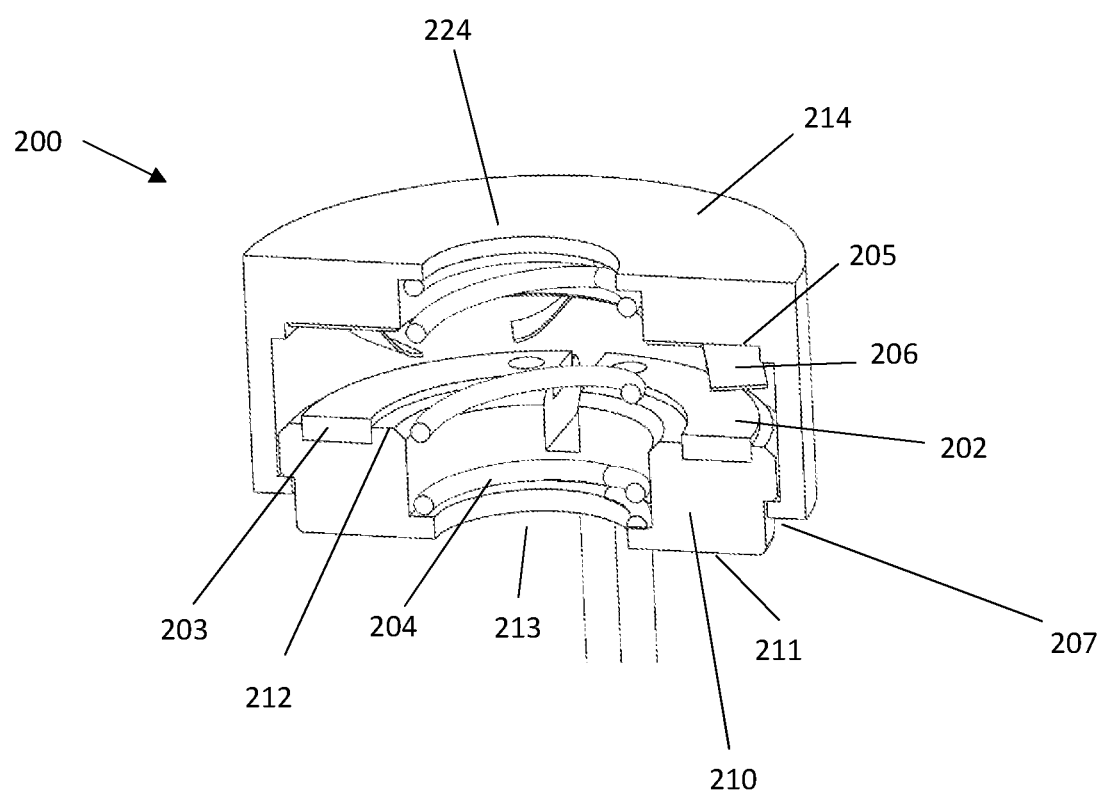
FIG. 5 is a perspective cross section view of the contact sensor.
Figure 6:
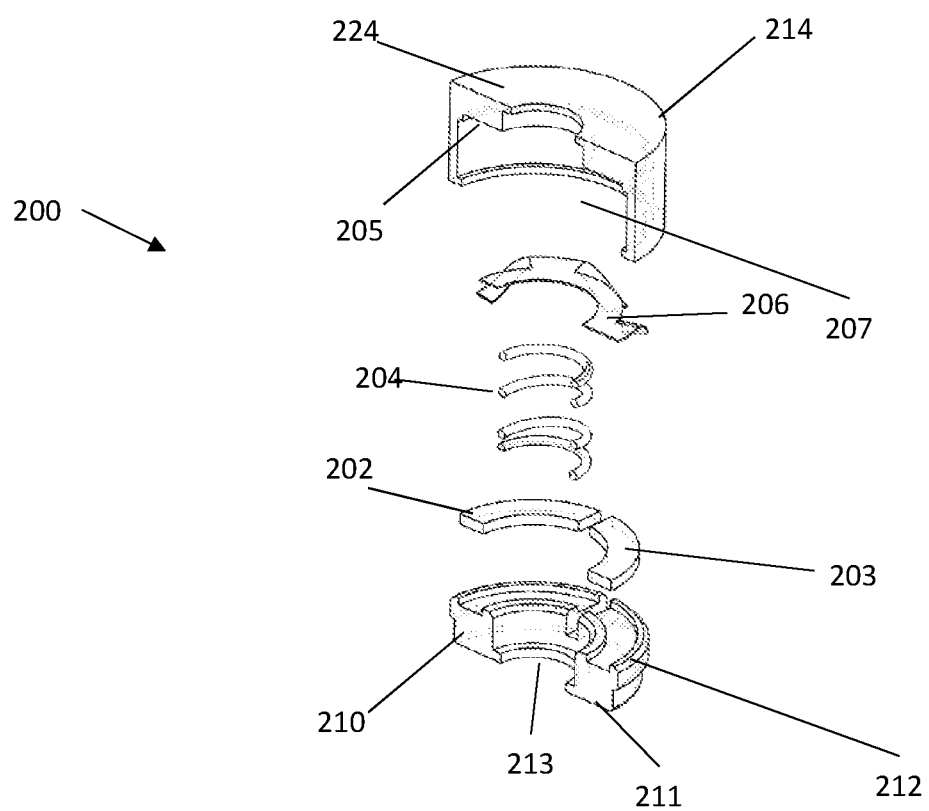
FIG. 6 is a perspective cross section exploded view of the contact sensor.
Figure 8:
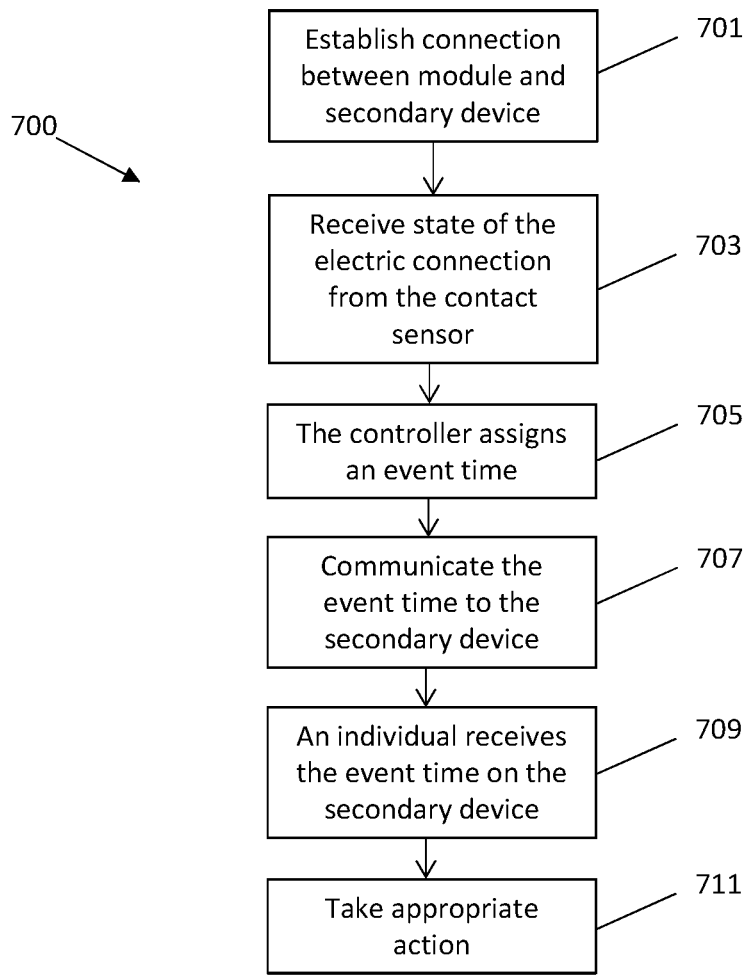
FIG. 8 is a flow chart of a method of use of the system.

Referring to FIG. 8, a flowchart is presented in accordance with an example method 700 of using the system 100. The method 700 is provided by way of example, as there are a variety of methods to use the system 100. Each block shown in FIG. 5 represents one or more processes, methods or subroutines, carried out in the example method 700. Furthermore, the illustrated order of blocks is illustrative only and the order of the blocks can change according to the present disclosure. Additional blocks may be added or fewer blocks may be utilized, without departing from this disclosure.

The example method 700 is a method for monitoring a fluid flow path of a medication for parenteral administration from a medication reservoir to a subject, and alerting an individual of interest of any change in the status of the fluid flow path. The example method 700 can begin at block 701. At block 701, a connection is established between the controller 300 and a secondary device 400. At block 703, the state of the electric connection is received by the controller from the contact sensor. The state of the electrical connection can be the presence or absence of an electrical connection. At block 705, the controller assigns an event time, wherein each event time indicates the time of a change in the state of the electrical current. At block 707, the controller 300 communicates the event time to a secondary device 400. At block 709, an individual receives the event time on the secondary device. For instance the secondary device 400 can alert the individual when an even time is received. At block 711, the individual can take appropriate action based on the alert. For example, the individual can call instruct the patient to re-connect the medication device.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

As used herein, the terms "communication" and "communicate" may refer to the reception, receipt, transmission, transfer, provision, and/or the like, of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection (e.g., a direct communication connection, an indirect communication connection, and/or the like) that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. Alternatively, a first unit may be in communication with a second unit if at least one intermediary unit (e.g., a third unit located between the first unit and the second unit) processes information received from the first unit and communicates the processed information to the second unit.

As used herein, the term "computing device" may refer to one or more electronic devices that are operable to directly or indirectly communicate with or over one or more networks. The computing device may be a mobile device. As used herein, the term "mobile device" may refer to one or more portable electronic devices operable to communicate with one or more networks. As an example, a mobile device may include a cellular phone (e.g., a smartphone or standard cellular phone), a portable computer (e.g., a tablet computer, a laptop computer, etc.), a wearable device (e.g., a watch, pair of glasses, lens, clothing, and/or the like), a portable computer with no user interface, a personal digital assistant (PDA), and/or other like devices. The computing device may not be a mobile device, such as a desktop computer. Furthermore, the term "computer" may refer to any computing device that includes the necessary components to receive, process, and output data, and normally includes a display, a processor, a memory, an input device, and a network interface.

As used herein, the term "application" or "application program interface" (API) refers to computer code, a set of rules, or other data sorted on a computer-readable medium that may be executed by a processor to facilitate interaction between software components, such as a client-side front-end and/or server-side back-end for receiving data from the client. An "interface" refers to a generated display, such as one or more graphical user interfaces (GUIs) with which a user may interact, either directly or indirectly (e.g., through a keyboard, mouse, etc.).

As used herein, the term "medication" refers to any substance (in liquid form) that is used to treat a health condition experienced by the patient. Non-limiting examples of medication include chemo drugs, nutrition delivered in total parenteral nutrition (TPN), hemotherapy drugs such as doxorubicin, vincristine, cisplatin, and paclitaxel, antibiotics such as vancomycin, meropenem, and gentamicin, antifungal drugs such as micafungin and amphotericin, pain medications such as hydromorphone and morphine, drugs for low blood pressure such as dopamine, epinephrine, norepinephrine, and dobutamine, and immunoglobulin medications (IVIG)

As various changes could be made in the above-described systems without departing from the scope of the invention, it is intended that all matter contained in the above description and in the examples given below, shall be interpreted as illustrative and not in a limiting sense.

What is claimed is:

1. A system for monitoring a state of a fluid flow path in a medication delivery device, the system comprising:
   an electrical contact sensor comprising a single-piece enclosure comprising at least two electrical contacts, wherein the electrical contact sensor attaches around an outside surface of a portion of the medication delivery device at one end of a connection point within the fluid flow path, wherein the electrical contact sensor is not within the fluid flow path, wherein the electrical contact sensor is operable to communicate a state of an electrical connection, wherein the state of the electrical connection is a presence or absence of electrical current; and
   a controller in electrical communication with the electrical contact sensor, the controller comprising an input component operable to receive the state of the electrical connection communicated by the electrical contact sensor and at least one processor operable to assign one or more event times, wherein each event time indicates a time of a change in the state of the fluid flow path,
   wherein connecting the fluid flow path at the connection point causes a change in an electrical connection of the at least two electrical contacts thereby changing the state of the electrical connection.

2. The system of claim 1, wherein the electrical contact sensor further comprises at least one spring operable to bias the at least two electrical contacts from establishing the electrical connection.

3. The system of claim 2, wherein the single-piece enclosure comprises:
   an elongated body comprising a cavity, a proximal surface comprising a top surface, a bottom surface, and an orifice extending from the top surface to the bottom surface, and a distal opening; and
   a support comprising a distal surface, a proximal surface, a perimeter complementary to an inside perimeter of the elongated body, an orifice extending from the distal surface to the proximal surface of the support, wherein the orifice is concentric with the orifice in the elongated body, forming a channel extending from the orifice in the elongated body to the orifice in the support, wherein the support is operable to be displaced along a longitudinal axis within the elongated body.

4. The system of claim 3, wherein the electrical contact sensor is attached to the medication delivery device through the channel extending from the orifice in the elongated body to the orifice in the support.

5. The system of claim 3, wherein the at least two electrical contacts are attached to the proximal surface of the support in a shape operable to surround the orifice in the support.

6. The system of claim 5, wherein the at least one spring surrounds the channel and extends from the bottom surface of the elongated body to the proximal surface of the support, and wherein the at least one spring is operable to bias the support from the bottom surface of the elongated body.

7. The system of claim 5, wherein the single-piece enclosure further comprises an electrically conductive ring attached to the bottom surface of the elongated body, wherein the electrically conductive ring is operable to contact and establish the electrical connection between the at least two electrical contacts when connecting the fluid flow path through the channel causes the support, the single-piece enclosure, or both, to be displaced along the longitudinal axis, wherein an electrical connection signals connection of the fluid flow path.

8. The system of claim 1, wherein the medication delivery device further comprises a first section of tubing and a second section of tubing, the first section of tubing comprising a first end and a second end, wherein the first end of the first section of tubing is attached to and in fluid communication with a medication reservoir, the second section of tubing comprising a first end and a second end, wherein the first end of the second section of tubing is configured to attach to and be in fluid communication with a medication dispense assembly, and wherein the second end of the first section of tubing and the second end of the second section of tubing are configured to couple together at the connection point to form the fluid flow path between the medication reservoir and the medication dispense assembly.

9. The system of claim 1, wherein the electrical contact sensor is configured to attach around the outside surface at the connection point located between a medication reservoir and a first end of a first section of tubing, located between a medication dispense assembly and a first end of a second section of tubing, or connecting a second end the first section of tubing and a second end of the second section of tubing.

10. The system of claim 9, wherein the controller is further operable to communicate the one or more event times to a patient, a caretaker for the patient, or an individual monitoring administration of medication to a subject.

11. The system of claim 10, wherein the controller is operable to communicate the one or more event times to one or more secondary devices.

12. The system of claim 11, wherein the controller further comprises a transmitter operable to communicate the one or more event times to the one or more secondary devices wirelessly using a wireless communication protocol.

13. The system of claim 12, wherein the wireless communication protocol is selected from an NFC communication, a Radio-frequency identification (RFID) communication, Bluetooth, LTE, ZigBee, LoraWAN, or Wi-Fi.

14. The system of claim 13, wherein the one or more secondary devices is a cloud computing device or a mobile computing device such as a cellular phone, a portable computer, a wearable device, a portable computer with no user interface, and/or a personal digital assistant (PDA).

15. The system of claim 1, wherein an electrical connection signals connection of the fluid flow path and the absence of an electrical connection signals disconnection of the fluid flow path.

16. The system of claim 1, wherein the medication delivery device further comprises an intravenous dispense assembly.

17. An electrical contact sensor device for monitoring a state of a fluid flow path in a medication delivery device, the electrical contact sensor device comprising:
   a single-piece enclosure comprising at least two electrical contacts, wherein the electrical contact sensor device attaches around an outside surface of a portion of the medication delivery device at one end of a connection point within the fluid flow path, wherein the electrical contact sensor device is not within the fluid flow path; and
   at least one spring operable to bias the at least two electrical contacts from establishing an electrical connection,
   wherein a state of the electrical connection is a presence or absence of electrical current, and wherein connecting the fluid flow path at the connection point causes a change in connection of the at least two electrical contacts thereby changing the state of the electrical connection.

18. The electrical contact sensor device of claim 17, wherein the single-piece enclosure comprises:
- an elongated body comprising a cavity, a proximal surface comprising a top surface, a bottom surface, and an orifice extending from the top surface to the bottom surface, and a distal opening; and
- a support comprising a distal surface, a proximal surface, a perimeter complementary to an inside perimeter of the elongated body, an orifice extending from the distal surface to the proximal surface of the support, wherein the orifice is concentric with the orifice in the elongated body, forming a channel extending from the orifice in the elongated body to the orifice in the support, wherein the support is operable to be displaced along a longitudinal axis within the elongated body.

19. The electrical contact sensor device of claim 18, wherein the at least one spring surrounds the channel and extends from the bottom surface of the elongated body to the proximal surface of the support, and wherein the at least one spring is operable to bias the support from the bottom surface of the elongated body.

20. The electrical contact sensor device of claim 18, wherein an electrical connection signals the connection of the fluid flow path and the absence of an electrical connection signals disconnection of the fluid flow path.

* * * * *